(12) United States Patent
Gubler

(10) Patent No.: US 10,426,756 B2
(45) Date of Patent: Oct. 1, 2019

(54) MULTIVITAMIN CAPABLE OF BENEFICIAL GENE REGULATION THROUGH MICRORNA (MIRNA)

(71) Applicant: Performance Labs PTE. LTD., Singapore (SG)

(72) Inventor: Daniel Gubler, Orem, UT (US)

(73) Assignee: PERFORMANCE LABS PTE. LTD., Singapore (SG)

( * ) Notice: Subject to any disclaimer, the term of this patent is extended or adjusted under 35 U.S.C. 154(b) by 0 days.

(21) Appl. No.: 15/669,158

(22) Filed: Aug. 4, 2017

(65) Prior Publication Data
US 2018/0036279 A1    Feb. 8, 2018

Related U.S. Application Data

(60) Provisional application No. 62/370,893, filed on Aug. 4, 2016.

(51) Int. Cl.
| | |
|---|---|
| A61K 36/00 | (2006.01) |
| A61K 31/352 | (2006.01) |
| A23L 33/10 | (2016.01) |
| A23L 33/00 | (2016.01) |
| A61K 31/12 | (2006.01) |
| A61K 31/26 | (2006.01) |
| A61K 31/519 | (2006.01) |
| A61K 31/7048 | (2006.01) |
| A61K 36/73 | (2006.01) |
| A61K 36/752 | (2006.01) |
| A61K 36/87 | (2006.01) |
| A23L 33/105 | (2016.01) |

(52) U.S. Cl.
CPC ............ *A61K 31/352* (2013.01); *A23L 33/10* (2016.08); *A23L 33/105* (2016.08); *A23L 33/40* (2016.08); *A61K 31/12* (2013.01); *A61K 31/26* (2013.01); *A61K 31/519* (2013.01); *A61K 31/7048* (2013.01); *A61K 36/73* (2013.01); *A61K 36/752* (2013.01); *A61K 36/87* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 6,646,013 B1 * | 11/2003 | Barker ................ | A61K 36/76 424/756 |
| 2004/0005368 A1 * | 1/2004 | Mann .................. | A61K 31/198 424/725 |
| 2004/0077556 A1 * | 4/2004 | Chinery .............. | A61K 31/198 514/27 |

OTHER PUBLICATIONS

Chakrabarti et al, Green tea polyphenols modulate expression of specific microRNAs for induction of molecular mechanisms of apoptosis in malignant neuroblastoma SH-SY5Y and SK-N-DZ cells. Cancer Research, (Apr. 15, 2012) vol. 72, No. 8, Supp. (Year: 2012).*
Arola-Arnal, et al. "Proanthocyanidins modulate microRNA expression in human HepG2 cells" PLoS One, Oct. 5, 2011, vol. 6, No. 10, e25982, pp. 1-7 (entire document).
Boesch-Saadatmandi, et al. "Effect of quercetin on inflammatory gene expression in mice liver in vivo—role of redox factor 1, miRNA-122 and miRNA-125b" Pharmacol Res, Feb. 28, 2012, vol. 65, No. 5, pp. 523-530 (entire document).
Dhar, et al. "Reservatrol and prostate cancer: promising role for microRNAs" Mol Nutr Food Res, Jun. 29, 2011, vol. 55, No. 8, pp. 1219-1229 (entire document).
Gontero, et al. "A randomized double-blind placebo controlled phase I-II study on clinical and molecular effects of dietary supplements in men with precancerous prostatic lesions" Prostate, Apr. 20, 2015, vol. 75, No. 11, pp. 1177-1186 (entire document).
Lan, et al. "Sulforaphane enhances temozolomide-induced apoptosis because of down-regulation of miR-21 via Wnt/β-catenin signaling in glioblastoma" J Neuroshem, Jun. 11, 2015, vol. 134, No. 5, pp. 811-818 (entire document).
Lancon, et al. "Effects of dietary phtophenois on the expression of microRNAs involved in mammalian cell homeostasis" J Sci Food Agric, Jul. 11, 2013, vol. 93, No. 13, pp. 3155-3164 (entire document).
Milenkovic, et al. "Modulation of miRNA expression by dietary polyphenols in apoE deficient mice: a new mechanism of the action of polphenols" PloSOne, Jan. 10, 2012, vol. 7, No. 1, e29837, pp. 1-12.
Sun, et al. "Curcumin (diferuloylmethane) alters the expression profiles of microRNAs in human pancreatic cancer cells" Mol Cancer Ther, Mar. 17, 2008, vol. 7, No. 3, pp. 464-473 (entire document).
United States Patent & Trademark Office, International Search Report and Written Opinion of the International Searching Authority for PCT/US2017/045486 dated Oct. 24, 2017, 13 pp.
Wang, et al. "Ethanol exposure induces differential microRNA and target gene expression and teratogenic effects which can be suppressed by folic acid supplementation" Hum Reprod, Dec. 17, 2008, vol. 24, No. 3, pp. 562-579 (entire document).
Fortmann, et. al. "Vitamin and Mineral Supplements in the Primary Prevention of Cardiovascular Disease and Cancer: An Updated Systematic Evidence Review for the US Preventive Services Task Force" Ann. Intern. Med. 2013, 159, 824-834.
Guallar, et. al. "Enough is Enough: Stop Wasting Money on Vitamin and Mineral Supplements" Ann. Intern. Med. 2013, 159, 850-851.

(Continued)

*Primary Examiner* — Qiuwen Mi
(74) *Attorney, Agent, or Firm* — Edwin S. Flores; Daniel J. Chalker; Chalker Flores, LLP

(57) ABSTRACT

The present invention includes compositions and methods for modifying the expression of microRNAs comprising: one or more plant secondary metabolites capable of beneficially regulating different genes in the human genome by modifying the expression of one or more microRNAs, wherein the one or more plant secondary metabolites are selected and provided in an amount selected to target the modification of one or more specific microRNA.

12 Claims, No Drawings

(56) References Cited

OTHER PUBLICATIONS

National Institutes of Health "National Institutes of Health State-of-the-Science Conference Statement: Multivitamin/Mineral Supplements and Chronic Disease Prevention" Am. J. Clin. Nutr. 2007, 85, 257S-264S.
Neuhouser, et. al. "Multivitamin Use and Risk of Cancer and Cardiovascular Disease in the Women's Health Initiative Cohorts" Arch. Intern. Med. 2009, 169 (3), 294-304.

* cited by examiner

MULTIVITAMIN CAPABLE OF BENEFICIAL GENE REGULATION THROUGH MICRORNA (MIRNA)

CROSS-REFERENCE TO RELATED APPLICATIONS

This application claims priority to U.S. Provisional Application Ser. No. 62/370,893, filed Aug. 4, 2016, the contents of which are incorporated by reference herein in its entirety.

STATEMENT OF FEDERALLY FUNDED RESEARCH

Not applicable.

TECHNICAL FIELD OF THE INVENTION

The present invention relates in general to the field of nutritional supplements, and more particularly, to nutritional supplements designed specifically to change gene expression levels by RNA interference.

BACKGROUND OF THE INVENTION

Without limiting the scope of the invention, its background is described in connection with nutritional supplements.

The multivitamin is the iconic and top selling nutritional supplement, with first versions showing up on the market in the 1940s. National Institutes of Health State-of-the-Science Conference Statement: Multivitamin/Mineral Supplements and Chronic Disease Prevention. Am. J. Clin. Nutr. 2007, 85, 257S-264S. Worldwide sales of multivitamins were estimated at 30 billion in 2015 and accounted for 60% of sales in the global nutritional supplement market. Although no health claims are specifically associated with multivitamins, most people (and industry marketing/education) imply multivitamin intake with decreased risk of both cancer and cardiovascular disease and improved cognition/performance.

Despite the preeminent stature of the multivitamin in the nutritional supplement market, the efficacy of the common multivitamin has been under recent attack. Several high profile studies have come out in recent years questioning the efficacy of the classic multivitamin. One of these was the study by Neuhouser et. al., who tracked multivitamin use in women with the risk of both cancer and cardiovascular disease. Neuhouser, et. al., Multivitamin Use and Risk of Cancer and Cardiovascular Disease in the Women's Health Initiative Cohorts. Arch. Intern. Med. 2009, 169 (3), 294-304. This study included 161,808 participants with continuous follow up for 8 years. The major takeaway, as summarized by the authors in their conclusion was as follows: "After a median follow-up of 8.0 and 7.9 years in the clinical trial and observational study cohorts, respectively, the Women's Health Initiative study provided convincing evidence that multivitamin use has little or no influence on the risk of common cancers, cardio vascular disease ("CVD"), or total mortality in postmenopausal women".

Another study suggesting bad news for the classic multivitamin was published in 2013 by Fortmann, et. al. Fortmann, et. al. Vitamin and Mineral Supplements in the Primary Prevention of Cardiovascular Disease and Cancer: An Updated Systematic Evidence Review for the U.S. Preventive Services Task Force. Ann. Intern. Med. 2013, 159, 824-834. This study also included a large sample size (27,658) of participants and used sound methodology. The concluding paragraph of the article stated: "Limited evidence supports any benefit from vitamin and mineral supplementation for the prevention of cancer or CVD. Two trials found a small, borderline-significant benefit from multivitamin supplements on cancer in men only and no effect on CVD."

The above cited papers and others prompted a widely shared editorial authored by medical doctors at the prestigious Johns Hopkins School of Medicine. Guallar, et. al. Enough is Enough: Stop Wasting Money on Vitamin and Mineral Supplements. Ann. Intern. Med. 2013, 159, 850-851. The authors summarized their key point of the editorial in the last paragraph of the article as follows: "Although available evidence does not rule out small benefits or harms or large benefits or harms in a small subgroup of the population, we believe that the case is closed—supplementing the diet of well-nourished adults with (most) mineral or vitamin supplements has no clear benefit and might even be harmful. These vitamins should not be used for chronic disease prevention. Enough is enough." Thus, a need remains for nutritional supplements designed specifically to overcome the problems in the prior art.

SUMMARY OF THE INVENTION

In one embodiment, the present invention includes a composition for modifying the expression of microRNAs comprising: one or more plant secondary metabolites capable of beneficially regulating different genes in the human genome by modifying the expression of one or more microRNAs, wherein the one or more plant secondary metabolites are selected and provided in an amount selected to target the modification of one or more specific microRNAs. In one aspect, the plant secondary metabolite is selected from at least 2, 3, 4, 5, 6, 7, 8, 9, or 10 plant secondary metabolites selected from epigallocatechin gallate; isoquercetin; folic acid; curcumin; hesperidin; grape polyphenols; sulporaphane; proanthocyanidins; apple polyphenols; or citrus bioflavonoids. In another aspect, the composition is in capsule, tablet, gel, powder, pill, granules, solution, suspension, softgel, gummy, chewable, liquid, cake, paste, fast melting tablet, film, bead, or bar form. In another aspect, the composition further comprises at least one of one or more nutritional or therapeutic excipients, salts, corrigents, fillers, buffers, diluents, binders, lubricants, sweeteners, coloring agents, flavoring agents, emulsifiers, stabilizers, glidants, or disintegrants. In another aspect, the expression of the microRNAs increased is selected from at least one of miR-7-1, miR-34a, miR-99, miR-122, miR-146a, miR-106a, miR106b, miR-17, miR-20a, miR-575, miR-483, miR-654, or miR-663. In another aspect, the expression of the microRNA decreased is selected from at least one miR-92, miR-93, miR-106b, miR-17, or miR-106a. In another aspect, the plant secondary metabolites are: epigallocatechin gallate (from green tea) in an amount of 70-300 milligrams; isoquercetin in an amount of 20-50 milligrams; folic acid in an amount of 150-350 micrograms; curcumin in an amount of 30-70 milligrams; hesperidin in an amount of 30-70 milligrams; grape polyphenols in an amount of 100-150 milligrams; sulporaphane in an amount of 0.2-2 milligrams; proanthocyanidins (from cranberry) in an amount of 45-70 milligrams; apple polyphenols in an amount of 65-90 milligrams; and citrus bioflavonoids in an amount of 80-110 milligrams. In another aspect, the composition further comprises a sweetener that is selected from at least one of sugar, saccharine, sucralose, aspartame, acesulfame potassium, stevia, and combinations thereof. In another aspect, the composition further comprises a flavorant selected from at least one of vanilla extract, cocoa powder, artificial vanilla flavorant, artificial chocolate flavorant, cream, dried cream extracts, caramel, and combinations thereof. In another aspect, the plant secondary metabolite is epigallocatechin and is provided in an amount that upregulates miR-16, miR-7-1, miR-34a, miR-210, and miR-99a and downregulate miR-92, miR-93, and miR-106b. In another aspect, the plant secondary metabolite is isoquercetin and is provided in an amount that upregulates miR-122, miR-125b, miR-146a, and changes the expression of miR-146, miR-125, miR-26, and miR-17. In another aspect, the plant secondary metabolite is folic acid and is provided in an amount that upregulates miR-122a and miR-125b, and down-regulate miR-10a, and miR-222. In another aspect, the plant secondary metabolite is curcumin and is provided in an amount that upregulates miR-22, and down-regulate miR-199a to modify expression of at least one of NF-κB, Akt, and MAPK. In another aspect, the plant secondary metabolite is hesperidin and is provided in an amount that upregulates miR-291b and miR-296, and down-regulate miR-30c, miR-467b, and miR-374. In another aspect, the plant secondary metabolite is grape polyphenols and is provided in an amount that upregulates miR-106a, miR-106b, miR-17, miR20a, miR-20b, miR-575, miR-483, miR-663, and miR-654, and down-regulate miR-17-92 and miR-106ab. In another aspect, the plant secondary metabolite is sulforaphane and is provided in an amount that upregulates miR-200c, and down-regulate miR-21. In another aspect, the plant secondary metabolite is proanthocyanidin and is provided in an amount that upregulates miR-197, miR-1224-3p, miR-532-3p, miR-483, and down-regulate miR-30b. In another aspect, the plant secondary metabolite is apple polyphenol and is provided in an amount that upregulates miR-106a, miR-106b, miR-17, miR20a, miR-20b, miR-575, miR-483, miR-663, and miR-654, and down-regulate miR-17-92 and miR-106ab. In another aspect, the plant secondary metabolite is citrus bioflavonoid and is provided in an amount that upregulates miR-7-1, miR-34a, miR-99a, miR-26a, miR-34c, and miR-146, and down-regulate mir-92, miR-93, mir-106b and miR-196.

In another embodiment, the present invention includes method of modifying the expression of one or more microRNAs in a subject comprising the steps of: identifying one or more beneficially regulated genes in the human genome; preparing a nutritional composition that comprises one or more plant secondary metabolites capable of beneficially regulating different genes in the human genome by modifying the expression of one or more microRNAs; and modifying the expression of one or more microRNAs with the nutritional composition. In another aspect, the plant secondary metabolite is epigallocatechin and is provided in an amount that upregulates miR-16, miR-7-1, miR-34a, miR-210, and miR-99a and downregulate miR-92, miR-93, and miR-106b. In another aspect, the plant secondary metabolite is isoquercetin and is provided in an amount that upregulates miR-122, miR-125b, miR-146a, and changes the expression of miR-146, miR-125, miR-26, and miR-17. In another aspect, the plant secondary metabolite is folic acid and is provided in an amount that upregulates miR-122a and miR-125b, and down-regulate miR-10a, and miR-222. In another aspect, the plant secondary metabolite is curcumin and is provided in an amount that upregulates miR-22, and down-regulate miR-199a to modify expression of at least one of NF-κB, Akt, and MAPK. In another aspect, the plant secondary metabolite is hesperidin and is provided in an amount that upregulates miR-291b and miR-296, and down-regulate miR-30c, miR-467b, and miR-374. In another aspect, the plant secondary metabolite is grape polyphenols and is provided in an amount that upregulates miR-106a, miR-106b, miR-17, miR20a, miR-20b, miR-575, miR-483, miR-663, and miR-654, and down-regulate miR-17-92 and miR-106ab. In another aspect, the plant secondary metabolite is sulforaphane and is provided in an amount that upregulates miR-200c, and down-regulate miR-21. In another aspect, the plant secondary metabolite is proanthocyanidin and is provided in an amount that upregulates miR-197, miR-1224-3p, miR-532-3p, miR-483, and down-regulate miR-30b. In another aspect, the plant secondary metabolite is apple polyphenol and is provided in an amount that upregulates miR-106a, miR-106b, miR-17, miR20a, miR-20b, miR-575, miR-483, miR-663, and miR-654, and down-regulate miR-17-92 and miR-106ab. In another aspect, the plant secondary metabolite is citrus bioflavonoid and is provided in an amount that upregulates miR-7-1, miR-34a, miR-99a, miR-26a, miR-34c, and miR-146, and down-regulate mir-92, miR-93, mir-106b and miR-196. In another aspect, the method further comprises the step of determining the level of expression of one or more microRNAs, providing the composition to the subject that targets changes in the expression of microRNAs, and measuring changes in the expression of the target microRNA after use of the composition by the subject to determining the effectiveness of the composition.

In another aspect, the plant secondary metabolite is selected from at least 2, 3, 4, 5, 6, 7, 8, 9, or 10 plant secondary metabolites selected from epigallocatechin gallate; isoquercetin; folic acid; curcumin; hesperidin; grape polyphenols; sulporaphane; proanthocyanidins; apple polyphenols; or citrus bioflavonoids.

In another embodiment, the present invention includes a method of changing a composition for changing the expression of one or more microRNAs, the method comprising: (a) measuring the expression of one or more target microRNAs from cells or tissue from a set of patients; (b) administering a composition comprising an amount of one or more plant secondary metabolites sufficient to beneficially regulating the expression of the one or more target microRNAs in a first subset of the patients, and a placebo to a second subset of the patients; (c) repeating step (a) after the administration of the composition or the placebo; and (d) determining if the composition increases the expression of certain target microRNAs, decreases the expression of the one or more target microRNAs, or both, that is statistically significant as compared to any reduction occurring in the second subset of patients, wherein a statistically significant reduction indicates that the composition is useful for changing microRNA expression.

Yet another embodiment of the present invention includes a nutritional supplement for modifying the expression of one or more specific microRNAs comprising: one or more plant secondary metabolites capable of beneficially regulating different genes in the human genome by modifying the expression of the one or more specific microRNA, wherein the one or more plant secondary metabolites are selected and provided in an amount selected to target the modification of one or more the one or more specific microRNAs. In one aspect, the plant secondary metabolites are selected from at least 2, 3, 4, 5, 6, 7, 8, 9, or 10 plant secondary metabolites selected from epigallocatechin gallate; isoquercetin; folic acid; curcumin; hesperidin; grape polyphenols; sulporaphane; proanthocyanidins; apple polyphenols; or citrus bioflavonoids. In another aspect, the composition is in capsule, tablet, gel, powder, pill, granules, solution, suspension, softgel, gummy, chewable, liquid, cake, paste, fast melting tablet, film, bead, or bar form. In another aspect, the composition further comprises at least one of one or more nutritional or therapeutic excipients, salts, corrigents, fillers, buffers, diluents, binders, lubricants, sweeteners, coloring agents, flavoring agents, emulsifiers, stabilizers, glidants, or disintegrants. In another aspect, the expression of the one or more specific microRNAs increased is selected from at least one of miR-7-1, miR-34a, miR-99, miR-122, miR-146a, miR-106a, miR106b, miR-17, miR-20a, miR-575, miR-483, miR-654, or miR-663. In another aspect, the expression of the one or more specific microRNAs decreased is selected from at least one of miR-92, miR-93, miR-106b, miR-17, or miR-106a.

BRIEF DESCRIPTION OF THE DRAWINGS

Not applicable.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention relates to the use of a unique combination/composition of different plant secondary metabolites capable of beneficially regulating different genes in the human genome whose mode of action is through microRNA (miRNA). The application of this invention in the nutraceutical industry is to create a next generation multivitamin with proven efficacy through legitimate science.

The present invention is based on the need to overcome the negative press and science regarding the effectiveness of the classic multivitamin, it is abundantly clear that humanity still needs the concept of a daily supplement to combat major issues that can compromise human health. These issues include, poor diet, lack of physical activity, lack of sleep, increased stress, living a fast paced lifestyle, environmental pollution, soil depletion, and many other factors.

Therefore, the present inventor has taken the general concept of the multivitamin, which is unquestionably sounds, but reevaluated it in light of the science behind changes in gene expression at the molecular level, and completely designed the ingredients included of the classic multivitamin. Specifically, the ingredients that comprise the makeup of the classic multivitamin include the vitamins and minerals found in fruits, vegetables, and other healthy foods. While vitamins and minerals are essential for human health, recent studies (along with those mentioned above) have shown, due to fortification of food products, that the average person obtains ample daily amounts of the vitamins/minerals deemed necessary for health.

If it isn't the vitamins/minerals alone from the vegetables and fruits we eat that are conferring a beneficial effect, the key question becomes is there something else in the healthy foods humans eat that is responsible for the health benefits of a multivitamin? Scientific research has shown that fruits, vegetables, and other healthy foods, in addition to containing vitamins/minerals, are rich in plant secondary metabolites or phytochemicals. These are organic compounds produced by the plants that have many roles including protection, communication, and potentially a number of other roles that are currently not well-studied and understood.

Plant secondary metabolites have also been questioned on what role, if any, these compounds play in human nutrition. Published research has shown that plant secondary metabolites (like polyphenols) play a major role in properly regulating the genes in the human body. The following two paragraphs give a brief primer on the basics of gene expression and its implications for human health.

A gene is a segment of DNA (the blueprint of life) that encodes for a protein—which constitute the machinery of the cells and are responsible for catalyzing the 10,000 different classes of chemical reactions the body performs every single second. All of the genes in an organism make up what is called its genome. Findings from the Human Genome Project have confirmed that the human genome consists of approximately 20,000 genes.

Each of the genes in the body can be thought of as a chemical switch that turns ON or OFF different enzymatic and signal transduction pathways in the body. In a properly functioning body each of these chemical switches is turned ON at certain points in time and is turned OFF at others. Disease state occurs when one or more of these chemical switches are broken and is stuck in either the ON or OFF position. This is a result of misregulated gene expression—meaning that the chromatin is permanently unwound, thus allowing the gene to be continuously transcribed or the chromatin is in its coiled-coiled closed structure and will not unwind so transcription and subsequent translation can occur.

The most important finding pertinent to this current invention is that certain secondary metabolites, like polyphenols, have the ability to fix or repair these broken genes (i.e., chemical switches) and bring them back into working order. The scientific literature (like the papers attached in the supporting information section) is replete with findings showing the ability of certain plant secondary metabolites to have chemopreventative properties. This is not surprising—as the underlying genetic basis for most forms of cancer is misregulated gene expression.

The currently accepted mode of action for the ability of plant secondary metabolites to beneficially regulate gene expression is through microRNA (miRNA). miRNAs are small (~18-25 nucleotide), non-coding, single stranded RNAs that can either turn OFF genes by silencing of the mRNA or, in other cases, turn ON genes through post-transcriptional modifications.

A dosage unit for use of the gene regulating metabolites of the present invention, may be a single compound or mixtures thereof. The compounds may be mixed together, form ionic or even covalent bonds. The gene regulating metabolites of the present invention may be administered using dosage forms well known to those of ordinary skill in the nutraceutical arts. Depending on the particular location or method of delivery, different dosage forms, e.g., tablets, capsules, pills, powders, granules, gelcaps, elixirs, suspensions, syrups, and emulsions may be used to provide the gene regulating metabolites of the present invention to an subject in need of nutritional supplementation. The gene regulating metabolites may also be administered as any one of known salt forms.

For example, the gene regulating metabolites of the present invention may be included in a tablet. Tablets may contain, e.g., suitable binders, lubricants, disintegrating agents, coloring agents, flavoring agents, flow-inducing agents and/or melting agents. For example, oral administration may be in a dosage unit form of a tablet, gelcap, caplet or capsule, the active drug component being combined with an non-toxic, nutraceutically acceptable, inert carrier such as lactose, gelatin, agar, starch, sucrose, glucose, methyl cellulose, magnesium stearate, dicalcium phosphate, calcium sulfate, mannitol, sorbitol, mixtures thereof, and the like. Suitable binders for use with the present invention include: starch, gelatin, natural sugars (e.g., glucose or beta-lactose), corn sweeteners, natural and synthetic gums (e.g., acacia, tragacanth or sodium alginate), carboxymethylcellulose, polyethylene glycol, waxes, and the like. Lubricants for use with the invention may include: sodium oleate, sodium stearate, magnesium stearate, sodium benzoate, sodium acetate, sodium chloride, mixtures thereof, and the like. Disintegrators may include, e.g., starch, methyl cellulose, agar, bentonite, xanthan gum, mixtures thereof, and the like.

The gene regulating metabolites of the present invention may also be coupled to one or more soluble, biodegradable, bioacceptable polymers as carriers. Such polymers may include, e.g., polyvinylpyrrolidone, pyran copolymer, polyhydroxylpropylmethacrylamide-phenol, polyhydroxyethylasparta-midephenol, or polyethyleneoxide-polylysine substituted with palmitoyl residues, mixtures thereof, and the like. Furthermore, the gene regulating metabolites may be coupled one or more biodegradable polymers to achieve controlled release of the gene regulating metabolites, biodegradable polymers for use with the present invention include: polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

In one embodiment, gelatin capsules (gelcaps) may include the gene regulating metabolites and powdered carriers, such as lactose, starch, cellulose derivatives, magnesium stearate, stearic acid, and the like. Like diluents may be used to make compressed tablets. Both tablets and capsules may be manufactured as immediate-release, mixed-release or sustained-release formulations to provide for a range of release of medication over a period of minutes to hours. Compressed tablets may be sugar coated or film coated to mask any unpleasant taste and protect the tablet from the atmosphere. An enteric coating may be used to provide selective disintegration in, e.g., the gastrointestinal tract.

For oral administration in a liquid dosage form, the oral drug components may be combined with any oral, non-toxic, nutraceutically acceptable inert carrier such as ethanol, glycerol, water, and the like. Examples of suitable liquid dosage forms include solutions or suspensions in water, nutraceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, thixotropic agents, organoleptic agents, diluents, sweeteners, thickeners, and melting agents, mixtures thereof, and the like.

Liquid dosage forms for oral administration may also include coloring and flavoring agents that increase patient acceptance and therefore compliance with a dosing regimen. In general, water, a suitable oil, saline, aqueous dextrose (e.g., glucose, lactose and related sugar solutions) and glycols (e.g., propylene glycol or polyethylene glycols) may be used as suitable carriers for parenteral solutions. Solutions for parenteral administration include generally, a water-soluble salt of the active ingredient, suitable stabilizing agents, and if necessary, buffering salts. Antioxidizing agents such as sodium bisulfite, sodium sulfite and/or ascorbic acid, either alone or in combination, are suitable stabilizing agents. Citric acid and its salts and sodium EDTA may also be included to increase stability. In addition, parenteral solutions may include nutraceutically acceptable preservatives, e.g., benzalkonium chloride, methyl- or propyl-paraben, and/or chlorobutanol.

Capsules. Capsules may be prepared by filling standard two-piece hard gelatin capsules each with 10 to 500 milligrams of powdered active ingredient, 5 to 150 milligrams of lactose, 5 to 50 milligrams of cellulose and 6 milligrams magnesium stearate.

Soft Gelatin Capsules. A mixture of active ingredient is dissolved in a digestible oil such as soybean oil, cottonseed oil or olive oil. The active ingredient is prepared and injected by using a positive displacement pump into gelatin to form soft gelatin capsules containing, e.g., 100-500 milligrams of the active ingredient. The capsules are washed and dried.

Tablets. A large number of tablets are prepared by conventional procedures so that the dosage unit was 100-500 milligrams of active ingredient, 0.2 milligrams of colloidal silicon dioxide, 5 milligrams of magnesium stearate, 50-275 milligrams of microcrystalline cellulose, 11 milligrams of starch and 98.8 milligrams of lactose. Appropriate coatings may be applied to increase palatability or delay absorption.

To provide an effervescent tablet appropriate amounts of, e.g., monosodium citrate and sodium bicarbonate, are blended together and then roller compacted, in the absence of water, to form flakes that are then crushed to give granulates. The granulates are then combined with the active ingredient, drug and/or salt thereof, conventional beading or filling agents and, optionally, sweeteners, flavors and lubricants.

Suspension. An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

For mini-tablets, the active ingredient is compressed into a hardness in the range 6 to 12 Kp. The hardness of the final tablets is influenced by the linear roller compaction strength used in preparing the granulates, which are influenced by the particle size of, e.g., the monosodium hydrogen carbonate and sodium hydrogen carbonate. For smaller particle sizes, a linear roller compaction strength of about 15 to 20 KN/cm may be used.

The present invention also includes kits useful, for example, for changing microRNA expression patterns, which comprise one or more containers containing one or more gene regulating metabolites composition comprising an effective amount of gene regulating metabolites. Such kits may further include, if desired, one or more of various conventional kit components, such as, for example, containers with one or more acceptable carriers, additional containers, etc., as will be readily apparent to those skilled in the art. Printed instructions, either as inserts or as labels, indicating quantities of the components to be administered, guidelines for administration, and/or guidelines for mixing the components, may also be included in the kit. It should be understood that although the specified materials and conditions are important in practicing the invention, unspecified materials and conditions are not excluded so long as they do not prevent the benefits of the invention from being realized.

A carrier for use with the gene regulating metabolites of the present invention can be a solid or liquid and the type is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents.

Examples of suitable liquid dosage forms include solutions or suspensions in water, nutraceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

The gene regulating metabolites may even be administered in the form of liposome delivery systems, e.g., small unilamellar vesicles, large unilamallar vesicles, and multi-lamellar vesicles, whether charged or uncharged. Liposomes may include one or more: phospholipids (e.g., cholesterol), stearylamine and/or phosphatidylcholines, mixtures thereof, and the like.

Details/Applications:

The ability of plant secondary metabolites to beneficially modulate the genes in the body is an area of research that is relatively unknown and is not currently utilized in the nutraceutical industry. The fact that the classical multivitamin has been labeled by competent medical professionals as "ineffective" and "a waste of money—at best" is likely due to the fact that despite containing efficacious amounts of vitamins/minerals, the classical multivitamin investigated in these studies was devoid of life-sustaining, gene-regulating secondary metabolites.

The fundamental tenants of the current invention, based on the ability of certain plant secondary metabolites to regulate gene expression via miRNA, are as follows:

In one embodiment, the present invention includes a multivitamin product that includes an efficacious and novel composition blend of secondary metabolites validated by the peer-reviewed scientific literature. This scientifically validated novel blend of gene regulating secondary plat metabolites, with amounts know to regulate gene expression is shown in Table 1 below.

TABLE 1

List of Compounds and Daily Intake Amounts of Gene Regulating Metabolites:

| Compound (or class of compound) | Dailey Amount Range |
|---|---|
| Epigallocatechin gallate (from Green Tea) | 70-300 milligrams |
| Isoquercetin | 20-50 milligrams |
| Folic Acid | 150-350 micrograms |
| Curcumin | 30-70 milligrams |
| Hesperidin | 30-70 milligrams |
| Grape Polyphenols | 100-150 milligrams |
| Sulporaphane | 0.2-2 milligrams |
| Proanthocyanidins (from Cranberry) | 45-70 milligrams |
| Apple Polyphenols | 65-90 milligrams |
| Citrus Bioflavonoids | 80-100 milligrams |

The finished product in this invention must include at least seven of the ten compounds listed in Table 1 above. Mode of action of the ability of these compounds to regulate the genes is through the interaction with microRNA. All materials used must be standardized to the bioactive compounds shown in Table 1. Generally, the expression of the microRNAs that can be modified are as follows: expression of the microRNAs increased is selected from at least one of miR-7-1, miR-34a, miR-99, miR-122, miR-146a, miR-106a, miR106b, miR-17, miR-20a, miR-575, miR-483, miR-654, or miR-663. In another embodiment, the expression of the microRNA decreased is selected from at least one miR-92, miR-93, miR-106b, miR-17, or miR-106a.

Generally, the gene regulating metabolite for use with the present invention will select one or more of the following metabolites for inclusion into a nutritional composition. Generally, the composition will include at least 2, 3, 4, 5, 6, 7, 8, 9, or 10 of the metabolites. For example, the following component will be added to regulate the listed microRNAs. For example, epigallocatechin is selected and provided in an amount to upregulate miR-16, miR-7-1, miR-34a, miR-210, and miR-99a and downregulate miR-92, miR-93, and miR-106b. In another example, isoquercetin is selected and provided in an amount to upregulate miR-122, miR-125b, miR-146a, and changes the expression of miR-146, miR-125, miR-26, and miR-17. In another example, folic acid is selected and provided in an amount to upregulate miR-122a and miR-125b, and down-regulate miR-10a, and miR-222. In another example, curcumin is selected and provided in an amount to upregulate miR-22, and down-regulate miR-199a to modify expression of at least one of NF-κB, Akt, and MAPK. In another example, hesperidin is selected and provided in an amount to upregulate miR-291b and miR-296, and down-regulate miR-30c, miR-467b, and miR-374. In another example, grape polyphenols are selected and provided in an amount to upregulate miR-106a, miR-106b, miR-17, miR20a, miR-20b, miR-575, miR-483, miR-663, and miR-654, and down-regulate miR-17-92 and miR-106ab. In another example, sulforaphane is selected and provided in an amount to upregulate miR-200c, and down-regulate miR-21. In another example, proanthocyanidin is selected and provided in an amount to upregulate miR-197, miR-1224-3p, miR-532-3p, miR-483, and down-regulate miR-30b. In another example, apple polyphenol is selected and provided in an amount to upregulate miR-106a, miR-106b, miR-17, miR20a, miR-20b, miR-575, miR-483, miR-663, and miR-654, and down-regulate miR-17-92 and miR-106ab. In another example, citrus bioflavonoid is selected and provided in an amount to upregulate miR-7-1, miR-34a, miR-99a, miR-26a, miR-34c, and miR-146, and down-regulate mir-92, miR-93, mir-106b and miR-196.

Thus, if a subject in need of nutritional supplementation sought to, or needed to, upregulate miR-7-1, miR-34a, miR-99a, miR-26a, miR-34c, and miR-146, and down-regulate mir-92, miR-93, mir-106b and miR-196, but also, upregulate miR-197, miR-1224-3p, miR-532-3p, miR-483, and down-regulate miR-30b, then citrus bioflavonoid and proanthocyanidin would be included in the composition. In one specific example, at least 7 of the components would be included in the composition. Other nutritional gene regulating metabolites can also be included depending on the microRNAs in need of up or down-regulating, as will be apparent to those of skill in the art based on the present disclosure.

These gene regulating metabolite compositions can be included with other standard vitamins and minerals found in the classic multivitamin. Finished product could be in capsule, tablet, gel, powder, softgel, gummy, liquid, or bar form. Further, non-natural metabolites or derivatives of the various components may also be used with the present invention. For example, active derivatives of epigallocatechin gallate, isoquercetin, folic acid, curcumin, hesperidin, grape polyphenols, sulporaphane, proanthocyanidins, apple polyphenols, and/or citrus bioflavonoids.

The development of this new composition that has the ability to beneficially regulate human gene expression is an inventive approach that can significantly increase the efficacy of the classic multivitamin.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A composition for modifying the expression of microRNAs comprising:
one or more plant secondary metabolites capable of beneficially regulating different genes in the human genome by modifying the expression of one or more microRNAs, wherein the one or more plant secondary metabolites are selected and provided in an amount selected to target the modification of one or more specific microRNAs, wherein the composition comprises the plant secondary metabolites:

epigallocatechin gallate in an amount of 70-300 milligrams;
isoquercetin in an amount of 20-50 milligrams;
folic acid in an amount of 150-350 micrograms;
curcumin in an amount of 30-70 milligrams;
hesperidin in an amount of 30-70 milligrams;
grape polyphenols in an amount of 100-150 milligrams;
sulforaphane in an amount of 0.2-2 milligrams;
proanthocyanidins in an amount of 45-70 milligrams;
apple polyphenols in an amount of 65-90 milligrams; and
citrus bioflavonoids in an amount of 80-110 milligrams.

2. The composition of claim 1, wherein the composition is in capsule, tablet, gel, powder, pill, granules, solution, suspension, softgel, gummy, chewable, liquid, cake, paste, fast melting tablet, film, bead, or bar form.

3. The composition of claim 1, wherein the composition further comprises at least one of one or more nutritional or therapeutic excipients, salts, corrigents, fillers, buffers, diluents, binders, lubricants, sweeteners, coloring agents, flavoring agents, emulsifiers, stabilizers, glidants, or disintegrants.

4. The composition of claim 1, wherein the expression of the microRNAs increased is selected from at least one of miR-7-1, miR-34a, miR-99, miR-122, miR-146a, miR-106a, miR106b, miR-17, miR-20a, miR-575, miR-483, miR-654, or miR-663.

5. The composition of claim 1, wherein the expression of the microRNA decreased is selected from at least one miR-92, miR-93, miR-106b, miR-17, or miR-106a.

6. The composition of claim 1, wherein the composition further comprises a sweetener which is selected from at least one of sugar, saccharine, sucralose, aspartame, acesulfame potassium, stevia, and combinations thereof.

7. The composition of claim 1, wherein the composition further comprises a flavorant selected from at least one of vanilla extract, cocoa powder, artificial vanilla flavorant, artificial chocolate flavorant, cream, dried cream extracts, caramel, and combinations thereof.

8. A nutritional supplement for modifying the expression of one or more specific microRNAs comprising:
one or more plant secondary metabolites capable of beneficially regulating different genes in the human genome by modifying the expression of the one or more specific microRNA, wherein the one or more plant secondary metabolites are selected and provided in an amount selected to target the modification of one or more the one or more specific microRNAs, wherein the supplement comprises the plant secondary metabolites obtained from two or more sources:
epigallocatechin gallate in an amount of 70-300 milligrams;
isoquercetin in an amount of 20-50 milligrams;
folic acid in an amount of 150-350 micrograms;
curcumin in an amount of 30-70 milligrams;
hesperidin in an amount of 30-70 milligrams;
grape polyphenols in an amount of 100-150 milligrams;
sulforaphane in an amount of 0.2-2 milligrams;
proanthocyanidins in an amount of 45-70 milligrams;
apple polyphenols in an amount of 65-90 milligrams; and
citrus bioflavonoids in an amount of 80-110 milligrams.

9. The nutritional supplement of claim 8, wherein the composition is in capsule, tablet, gel, powder, pill, granules, solution, suspension, softgel, gummy, chewable, liquid, cake, paste, fast melting tablet, film, bead, or bar form.

10. The nutritional supplement of claim 8, wherein the composition further comprises at least one of one or more nutritional or therapeutic excipients, salts, corrigents, fillers, buffers, diluents, binders, lubricants, sweeteners, coloring agents, flavoring agents, emulsifiers, stabilizers, glidants, or disintegrants.

11. The nutritional supplement of claim 8, wherein the expression of the one or more specific microRNAs increased is selected from at least one of miR-7-1, miR-34a, miR-99, miR-122, miR-146a, miR-106a, miR106b, miR-17, miR-20a, miR-575, miR-483, miR-654, or miR-663.

12. The nutritional supplement of claim 8, wherein the expression of the one or more specific microRNAs decreased is selected from at least one of miR-92, miR-93, miR-106b, miR-17, or miR-106a.

* * * * *